(12) United States Patent  (10) Patent No.: US 8,430,830 B1
Ariza  (45) Date of Patent: Apr. 30, 2013

(54) POST OPERATIVE PRESSURE GARMENT

(76) Inventor: Alfredo Ernesto Hoyos Ariza, Miami, FL (US)

( * ) Notice: Subject to any disclaimer, the term of this patent is extended or adjusted under 35 U.S.C. 154(b) by 136 days.

(21) Appl. No.: 13/046,402

(22) Filed: Mar. 11, 2011

Related U.S. Application Data

(63) Continuation-in-part of application No. 13/046,382, filed on Mar. 11, 2011, which is a continuation-in-part of application No. 12/287,817, filed on Oct. 14, 2008, now Pat. No. 8,105,256.

(51) Int. Cl.
*A61F 5/00* (2006.01)

(52) U.S. Cl.
USPC .................................. 602/19; 602/60; 602/61

(58) Field of Classification Search .............. 602/13, 602/23, 23.27, 60–62, 75, 19, 27; 128/882, 128/874–875; 450/20
See application file for complete search history.

(56) References Cited

U.S. PATENT DOCUMENTS

| | | | |
|---|---|---|---|
| 1,761,278 A * | 6/1930 | Redmond | ........................ 450/20 |
| 2,105,605 A | 1/1938 | Lichtenstein | |
| 2,505,720 A | 4/1950 | Peiser et al. | |
| 2,697,224 A | 12/1954 | Aidenland | |
| 5,158,531 A | 10/1992 | Zamosky | |
| 5,718,670 A | 2/1998 | Bremer | |
| 5,823,984 A | 10/1998 | Silverberg | |
| 6,276,175 B1 | 8/2001 | Browder, Jr. | |
| 6,585,673 B1 | 7/2003 | Bass | |
| 8,105,256 B1 | 1/2012 | Ariza | |
| 2002/0106970 A1 | 8/2002 | Falla | |
| 2010/0130903 A1 * | 5/2010 | Rock | ............................... 602/62 |

* cited by examiner

*Primary Examiner* — Michael A. Brown
(74) *Attorney, Agent, or Firm* — Malloy & Malloy, P.L.

(57) ABSTRACT

A compression garment for treating post operative patients involved in body contouring surgery and including a base structured for removable disposition in an operative position about the torso and other portions of the patient's body. The compression garment is dimensioned, configured and structured to apply appropriate compression to the surgically affected portions of the patient in order to reduce pain, diminish swelling and avoid fluid accumulation, while not impairing the venous and lymphatic circulation of the affected body portion. The base has one or a first and second cover member overlying its internal and external faces and a closure assembly serves to maintain the garment in a variable closed orientation such that appropriate compressive force may be applied to the affected body areas.

6 Claims, 7 Drawing Sheets

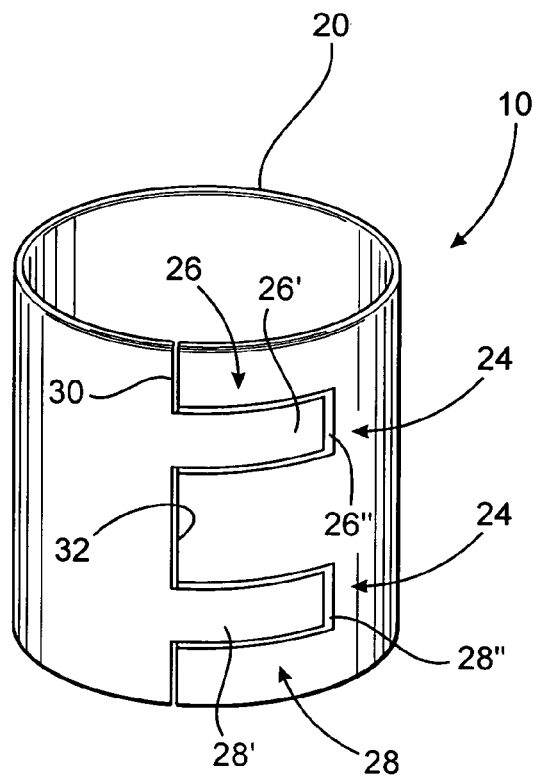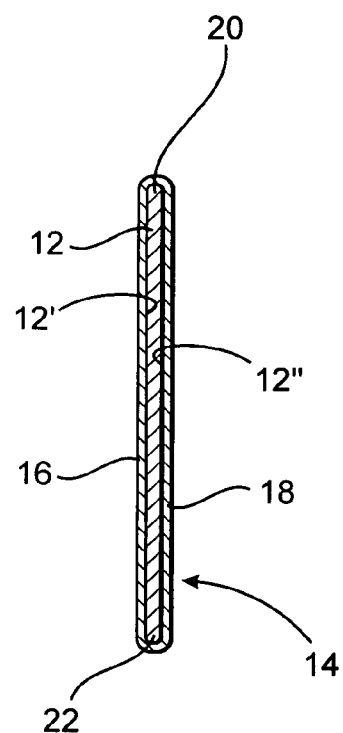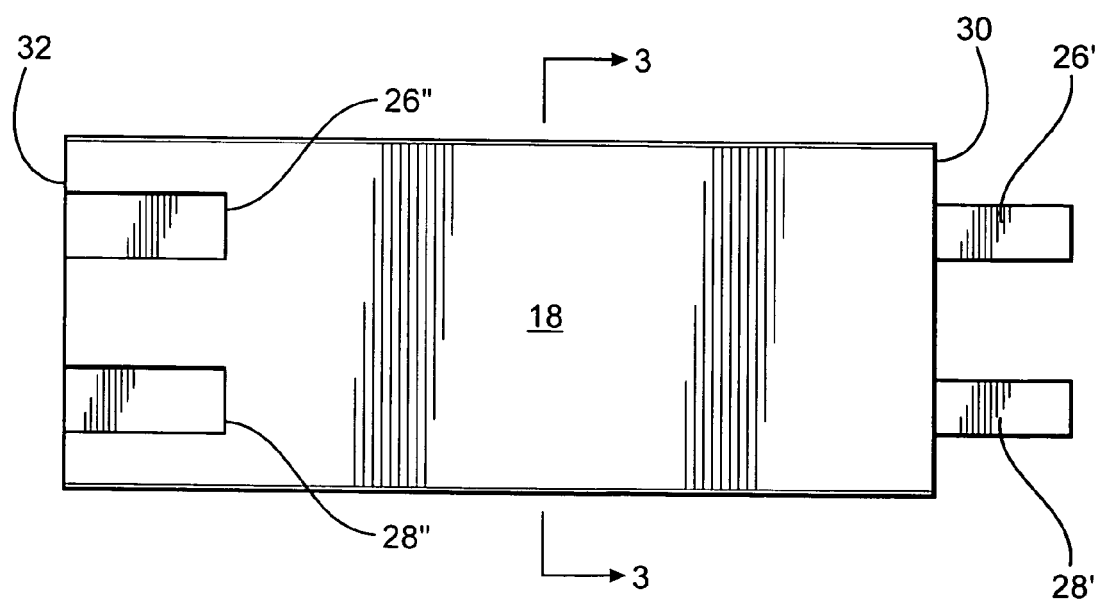

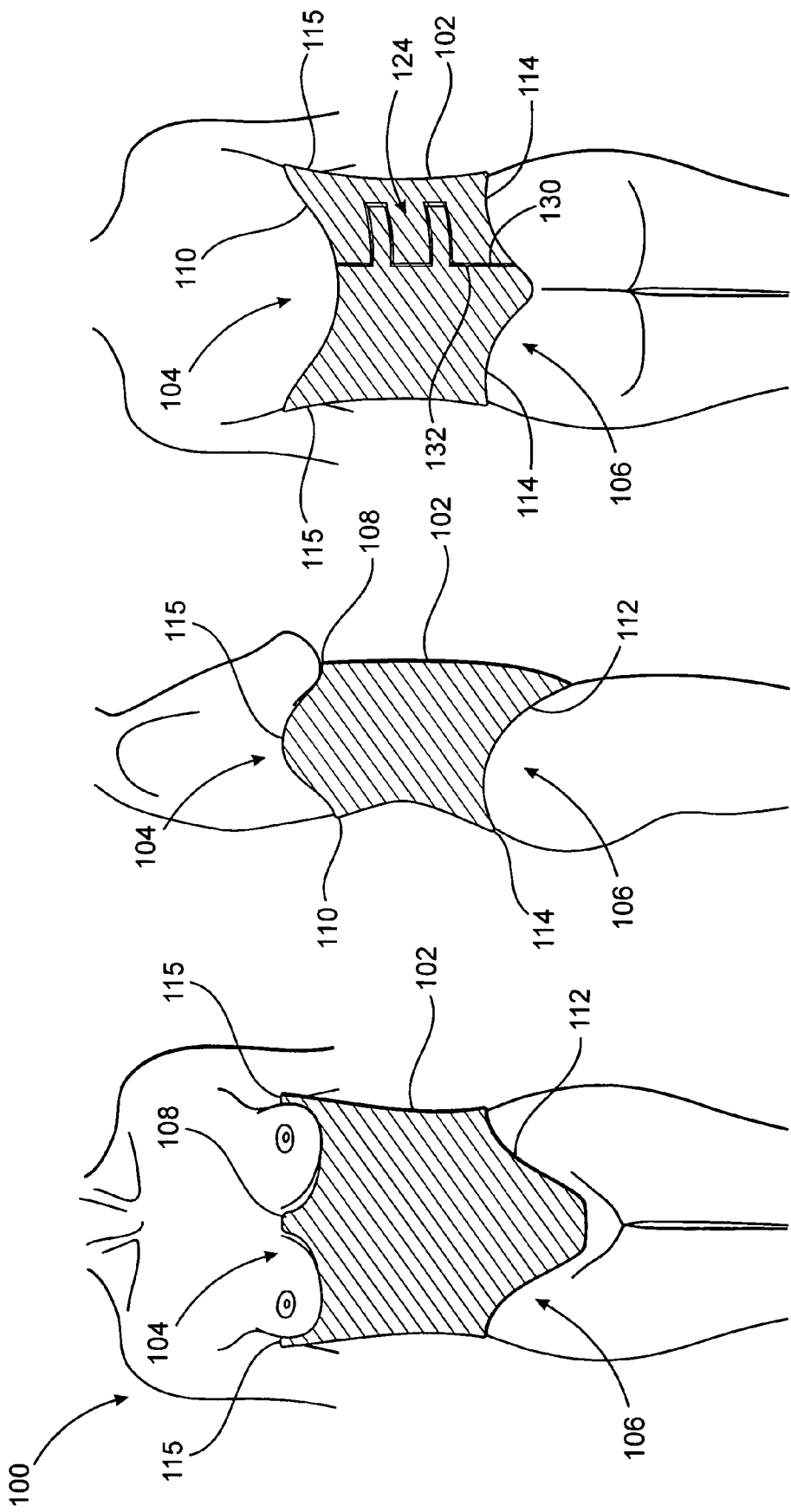

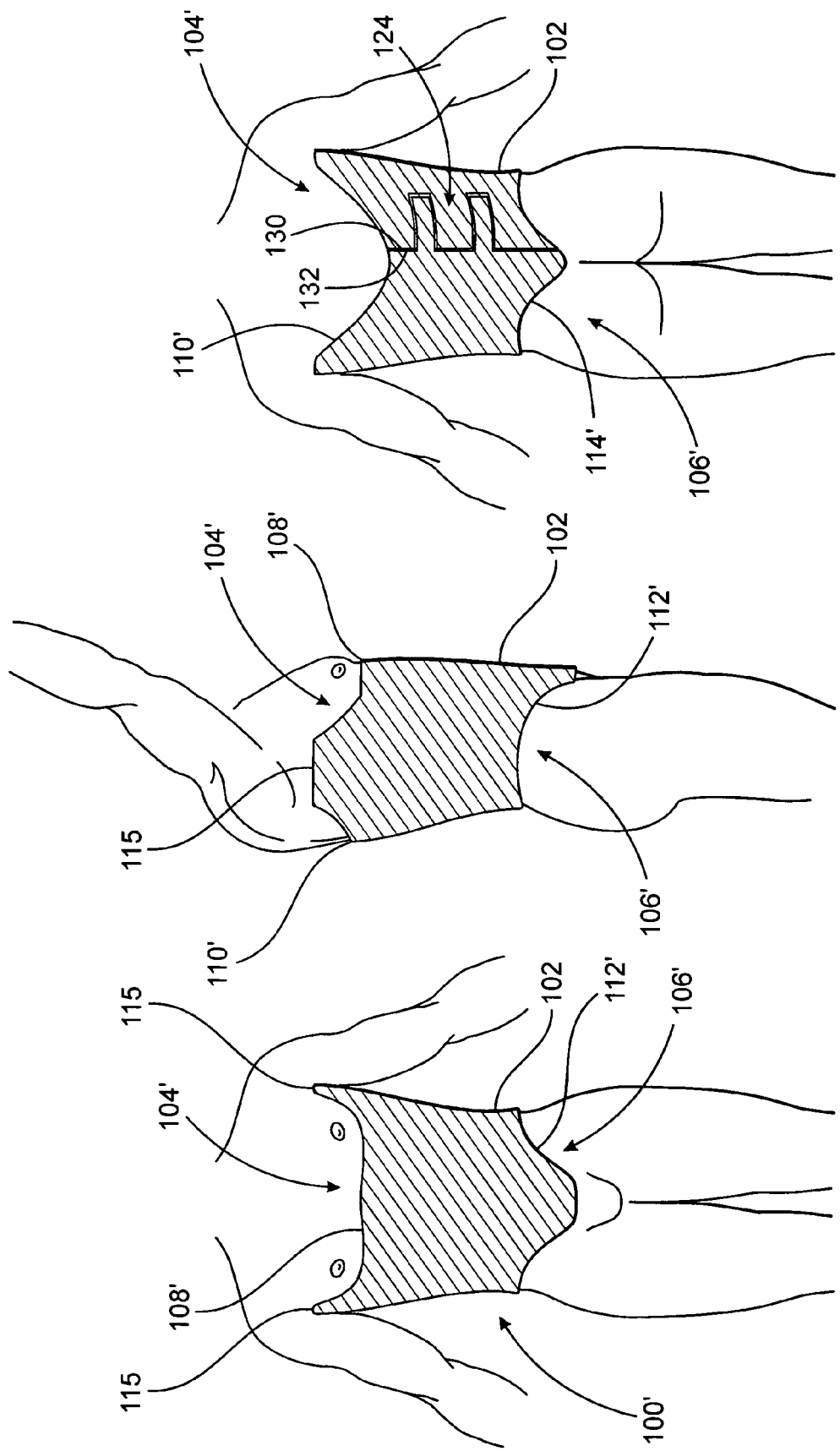

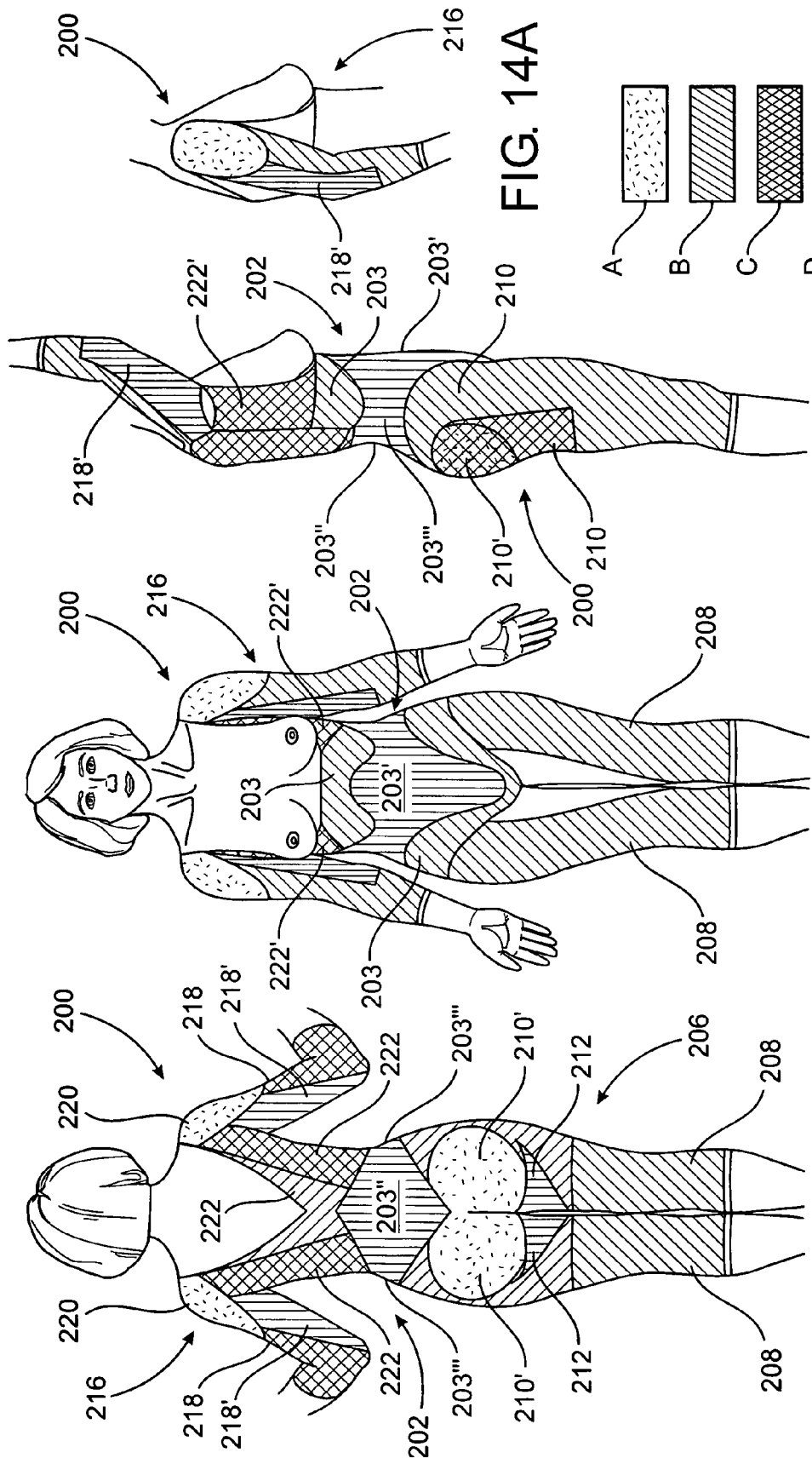

POST OPERATIVE PRESSURE GARMENT

CLAIM OF PRIORITY

The present application is a continuation-in-part application of previously filed, now pending application having Ser. No. 13/046,382, filed on Mar. 11, 2011, which is a continuation-in-part application of previously filed, application having Ser. No. 12/287,817, filed on Oct. 14, 2008 now U.S. Pat. No. 8,105,256 both of which are incorporated herein in their entirety by reference.

BACKGROUND OF THE INVENTION

1. Field of the Invention

The present invention is directed to a compression garment removably disposed on a post operative patient involved in body sculpting surgery. The compression garment is dimensioned and configured to assume an operative position and as such exert a predetermined, appropriate amount of compression on surgically affected portions including both the soft tissue and bony prominences of the patient's body in order to reduce pain, diminish swelling and avoid fluid accumulation.

2. Description of the Related Art

Lipoplasty or other body contouring surgery procedures has become increasingly popular and is commonly practiced in many medically advanced countries throughout the world. Subsequent to undergoing such surgical procedures, the patient frequently encounters pain, a relatively extended healing period due to swelling and the accumulation of fluids, commonly referred to as "seroma". In order to avoid or at least significantly reduce these problems, the patient is at least generally treated by subjecting the surgically affected areas of the body by the application of compressive forces. Typically, such compression must generally be less than 10 mm/hg. Compressive forces in this range are generally considered sufficient to reduce symptoms of the type set forth above but not enough to impair venous and/or lymphatic circulation.

However, conventionally available means to apply such compressive forces fail to consider the variations in the patient's body, such as, but not limited to the "bony areas or prominences" such as, but not limited to the iliac crest and/or the rib cage area. These areas of bony prominences, when subjected to the same compressive force as the soft tissue areas, are frequently subjected to abrasions and other injuries due to excessively high pressure being applied to these bony portions. In contrast, soft tissue portions of the patient's body, including the central part of the abdomen, are generally subjected to lower and sometimes inadequate compressive forces. This is due to a "tent" effect at least partially caused by the adjacent or surrounding bony prominences engaging the force generating structure applied to the patient's body. Accordingly, certain portions of the patient's body are under a lower compression and are accordingly more prone to develop complications, such as fluid retention and fibrosis.

Therefore there is a need in the medical profession for a device or assembly which is properly structured, dimensioned and configured to apply an appropriate compressive force to surgically treated portions of the patient's body. Such a proposed device should be applied during a post operative period so as to alleviate and/or significantly reduce discomfort to the patient by the reduction of pain, the diminishing of swelling and/or the avoidance of fluid accumulation, as generally set forth above. Further, such a proposed and preferred compressive generating device could, in at least one embodiment, comprise a compression garment secured in an appropriate closed orientation about the surgically treated portion of the patient's body in a manner which facilitates the application of the appropriate compressive forces. In addition, the structure of such a preferred compression garment should be such as to decrease the compressive forces applied to or in the area of the bony prominences, while increasing or applying the appropriate pressure on the soft tissue areas. The preferred compression garment would thereby prevent or reduce discomfort to the bony prominences while increasing the comfort and avoiding complications to the overall surgical site of the lipoplasty or other body contouring surgery.

Further, due to the advancement in body contouring surgical procedures, the surgically affected areas of the patient's body may involve a majority or substantial portion of the torso of the patient. As such, a preferred and proposed compression garment may preferably assume and be mounted on a post operative patient in a preferred operative position which may comprise, in certain applications, the surrounding of the entire torso area of the patient. Accordingly, when assuming such an operative position the compression garment is disposed in a closed orientation which is variable at least to the extent of accommodating patients of different sizes. However, an appropriate compressive force will be applied in surrounding relation to appropriate portions of the torso of the post operative patient.

Finally, the preferred and proposed compression garment may be applied directly to the outer surface or skin of the patient and may be disposed beneath an outer garment, wherein the mounting or removable securement to the patient may occur while the patient is standing, sitting or lying down, immediately after the surgical procedure. The versatility of such a preferred and proposed compression garment allows its use for relatively brief periods such as forty-eight hours post surgical procedure or as long as thirty days thereafter.

SUMMARY OF THE INVENTION

The present invention is directed to a compression garment used for post operative patients having been involved in any of a wide variety of body sculpting surgical procedures and including, but not limited to lipoplasty. Further, the compression garment assembly of the present invention is structured to overcome various problems and disadvantages associated with conventional or known post operative devices intended to apply some type of retaining or compressive force to surgically affected areas of a post operative patient. Accordingly, the structural and operative features of the compression garment of the present invention will serve to reduce pain and recovery time, by diminishing the swelling associated with the surgical procedure. In addition proper use and application of the compression garment assembly of the present invention will prevent the appearances of bruises conventionally associated with high pressure related complications when utilizing known or conventional devices of the type generally set forth above. The application of the compression garment of the present invention in a correct operative position will result in elimination of abrasions or skin necrosis. Moreover, the application of an appropriate compressive force to the surgically affected areas of the post operative patient can be maintained for any appropriate time period depending upon the specific type of body contouring surgery involved.

More specifically, the compression garment of the present invention includes a base or core formed of a flexible, compressible material such as, but not limited to, an economically, cost effective foam material. Such a preferred foam material from which the base is formed may include polystyrene foam which is relatively inexpensive. Such a foam material is adapted to accommodate varying degrees of compression to the bony prominences and the soft tissue through the application of lesser or greater amounts of compressive forces as appropriate.

In addition, a cover assembly is disposed in overlying covering relation to the flexible and compressible material base or core. As such, the cover assembly may include a first cover member disposed in overlying, covering relation to an internal face or surface of the core and which is disposed to come in to direct contact with the skin of the patient. In addition, the covering assembly may include a second cover member extending in overlying, covering relation to the outer face or surface of the foam material base. Variations in the structural features of the covering assembly, specifically including the first and second cover members, may include their formation from cotton or other appropriate, natural or synthetic material. Such material(s) should also be non-allergenic and/or otherwise structured to prevent complications when maintained in confronting engagement with the skin of the post operative patient for extended periods. Further, the first and second cover members may include an integral or otherwise fixedly attached interconnecting structure or may comprise a one piece structure disposed in substantially enclosing relation to the inner and outer faces or surfaces of the base, as well as the contiguously disposed peripheral portions or junctions thereof.

It is to be understood that the compression garment of the present invention may be manufactured and provided in various sizes to accommodate different individuals. In addition, the various preferred embodiments of the subject compression garment include a closure assembly which is preferably disposed at each of the opposite ends of the base. The closure assembly is structured to removably retain the base or core in a closed orientation while in an operative position, applying appropriate compressive force to the surgically affected areas of the patient's body. As will be described in greater detail hereinafter, the closed orientation may be defined in at least some of the preferred embodiments of the present invention as surrounding a majority or entirety of the torso of the patient, wherein the opposite ends are brought into a substantial or predetermined alignment with one another. Such an aligned relation of the opposite ends may comprise a variable overlapping disposition to one another. As such, an appropriate compressive force may be applied to the torso or other appropriate portion of the user's body depending on the size and shape of the engaged body portion. Further, the substantially aligned relation of the opposite ends may include a substantially adjacent or contiguous positioning of the opposite ends when in the closed orientation. Alternatively, the substantially aligned relation of the opposite ends may comprise an at least minimal spacing from one another, while still in the closed orientation and surrounding relation to the torso or other affected portions of the patient's body.

Accordingly, application of the compression garment of the present invention to a post operative patient in an operative position comprises a closed orientation thereof, wherein the base effectively surrounds the affected portions of the patient's body specifically including, but not limited to, the torso portion. The structural and operative features of the garment assembly facilitates a compressive force being applied in a manner which will accommodate the bony prominences of the body, through the application an appropriately lesser compressive force, while concurrently or simultaneously applying an appropriately greater compressive force to the soft tissue portions. As a result, the compression garment of the present invention will serve to reduce pain and recovery time by diminishing swelling in a post operative patient while preventing the occurrence of bruises or other skin abrasions. Moreover, the accumulation of fluids or the avoidance of seromas and hematomas will be accomplished while maintaining appropriate venous and lymphatic circulation.

As set forth in greater detail hereinafter, additional preferred embodiments of the present invention include a compression garment comprising an outer garment. The outer garment is structured to be used independently or, depending upon the needs and requirements of a patient, in overlying relation to an undergarment such as, but not limited to, an under compression garment, of the type set forth above. More specifically, the outer garment comprises a base structured for operative disposition in surrounding relation to at least a torso portion of the patient including when it is disposed in overlying relation an undergarment. In addition, the base includes a first end and a second end each extending along and at least partially defining a different periphery of the base. As such, the first end may also be defined as the upper end of the base and the second end may be accurately described as the lower end of the base. As used herein, the terms "upper" and "lower" are indicative of the location of the first end and second ends when the patient is in an upright, standing orientation or an upright sitting orientation. As such, the first or upper end will be located closer to the shoulders and head portion of the patient, wherein the second end or lower end will be located adjacent or closer to the hip portion of the patient.

In addition, the first end and the second end each include a frontal portion and a rear portion. The frontal portion of the first end extends across and in a substantially aligned relation with a lower pectoral region, when the base is operatively disposed. In contrast, the frontal portion of the second end extends across and in substantially aligned relation with the pelvic area and/or pubic area depending upon the specific configuration of the frontal portion of the second end. The rear portion of the upper, first end extends in overlying relation to a portion of the back of the patient, wherein the rear portion of the lower, second end preferably includes a scalloped configuration which extends across and conforms with the upper area of the buttocks region of the patient.

In addition, the base of the outer garment also includes at least two lateral portions substantially oppositely disposed in interconnecting relation between the frontal portion and rear portion of at least the first end. The lateral portions extend outwardly from the frontal and rear portions into a predetermined underarm position on the patient. As a result, an appropriate compressive force is exerted on the corresponding portions of the torso located under the patient's arms as desired. Moreover, each of the lateral portions has a sufficient longitudinal dimension to extend outwardly from the frontal and rear portions of the first end into a substantially aligned relation with a different "armpit" of the patient. Cooperatively, each of the lateral portions includes a sufficient transverse dimension to extend across a corresponding side of the patient's torso in attached relation to the frontal and rear portions of the first or upper end of the base of the undergarment, as generally set forth above.

Structural modifications of the embodiments of the outer garment include a dimensioning and configuring to render the base more adaptive to the body of a female, post operative patient or a male, post inoperative patient. Accordingly, one embodiment of the outer garment includes the frontal portion of the first or upper end having a substantially scalloped configuration extending along at least a majority of the first end between the two lateral portions. Moreover, the scalloped configuration is disposed and dimensioned to substantially conform to the lower pectoral region or breasts of a female patient. In contrast, the frontal portion of the first or upper end of a structurally modified base of the outer garment, intended for use by a male patient, includes a substantially linear configuration. The linear configuration of the "male" outer garment extends along at least a majority of the length between the lateral portions and also is disposed in substantially aligned relation with the typically less prominent, lower pectoral region of a male patient. Common to both the "male" and "female" outer garments is the rear portion of the second end each having a generally scalloped configuration which is dimensioned and configured to be aligned with and therefore substantially conformed to the upper buttocks region of the male and/or female patient.

In either of the male or female embodiments of the outer garment, the material from which at least a majority of the base is formed demonstrates compressive physical characteristics such as, but not limited to, a compressive foam material. In addition, each of the male and female outer garments includes a closure assembly attached to opposite free ends of the respective bases. The closure assembly is structured to removably maintain the corresponding base in a closed orientation, when operatively disposed in surrounding relation to the torso of the patient. Moreover, as with the above described undergarment, the closed orientation of the closure assembly is at least partially defined by it interconnecting and substantially aligning the opposite ends of the base. Further, the closed orientation may vary at least dependent on the size of the patient. Also, the degree of compression to be applied to the patient by the compressive, foam material base may vary or be adjusted, based on the position and closed orientation of the closure assembly. This variable compressive force may be accomplished whether the garment is used independently or in overlying relation to the above noted undergarment.

Therefore, application of the outer compression garment, whether used independently of or in overlying combination with an, undergarment facilitates a compressive force being applied in a manner which will accommodate both the boney protuberance of the body as well as the soft tissue portions of the body. The intended and preferred result will be the outer compression garment serving to reduce pain and recovery time by diminishing swelling in a post operative male or female patient, while reducing the possibility of bruises or other skin abrasions. As also set forth above, the accumulation of fluids and the avoidance of seromas and/or hematomas will be accomplished while maintaining appropriate venous and lymphatic circulation.

The present invention comprises yet additional preferred embodiments including an outer garment or garment assembly also structured to compress predetermined portions of a post operative patient. As such, these additional compression garment structures may be disposed on a patient's body and used as an outer garment either independently of or in overlying relation to an under compression garment such as, but not limited to, an undergarment of the type represented in FIGS. 1-5.

More specifically, the additional preferred embodiments comprise a torso section disposed in at least partially surrounding relation to the torso part of the patient. In addition, a lower section is disposed beneath the torso section and is structured to at least partially enclose the upper legs and buttocks of the patient. Additionally, an upper section is disposed above the torso section in at least partially enclosing and/or confronting relation to the arms and upper lateral portions of the patient. Additional structural and operative features of these preferred embodiments include the torso section, lower section and upper section each comprising a plurality of segments. Moreover, the plurality of segments of each of these sections are cooperatively disposed and structured to vary compressive force applied to body parts which are correspondingly disposed to the plurality of segments of each of the torso, lower and upper sections.

Accordingly, different body portions of a post operative patient are intended to be subjected to different degrees of compressive forces. Therefore, the plurality of segments of each of the torso, lower and upper sections are collectively structured to exert the plurality of different but predetermined degrees of compressive force collectively on the corresponding body parts of the patient with which the plurality of segments are associated. By way of example and as described in greater detail hereinafter, the cooperatively structured segments of each of the aforementioned torso, lower and upper sections may be independently but collectively structured to exert at least three and possibly more differing degrees of compressive force on the corresponding body sections.

The torso section may include an abdominal segment is disposed in confronting relation to the abdomen of the patient. The abdominal segment is structured to apply a greater degree of compressive force to the abdomen then at least some of a remainder of the plurality of segments associated with the torso section. In turn, the remainder of the plurality of segments of the torso section may be cooperatively structured to apply different degrees of compressive force to corresponding body portions, as compared to one another.

Somewhat similarly, the lower section of these additional preferred embodiments of the outer garment may include two gluteal segments each disposed in at least partially confronting relation to the buttocks and in at least partially aligned relation to a portion of a gluteal crease of the patient's buttocks. In turn, the plurality of segments associated with the upper section may include at least two underarm segments each extending along at least a majority of a length between a corresponding elbow and a corresponding shoulder and in overlying or confronting relation to a corresponding tricep area of the patient.

Further, while the plurality of segments of each of the torso, lower and upper sections may be structured to apply to different degrees of compressive force to corresponding body portions, the abdominal segment, gluteal segments and the under arm segments may be structured to apply a greater degree of compressive force to the corresponding body parts than a remainder of the plurality of segments associated with each of the torso, lower and upper sections. As such, the body section subjected to the greatest compressive force, such as the abdomen, buttocks and tricep areas of the patient, may be those areas which would mostly or more commonly benefit the patient by applying the increased or maximum compressive force. However, it is emphasized any of the plurality of segments associated with each of the plurality of torso, lower and upper sections may effectively be "customized". Such customization may result in the compressive force applied to the body parts of a patient being predetermined and at least partially dependent on the surgical procedure in which the patient participated.

As set forth hereinafter, the versatility of the garment assembly defining these preferred embodiments is demonstrated by their dimensioning, configuring and overall structuring in a manner which substantially conforms selectively to either the body of a female patient or male patient. Also, whether intended to conform to a female or male patient, the aforementioned sections being separately and independently secured in their intended operative position on the patient's body. In the alternative, at least two of the aforementioned sections or all three of the torso, lower, and upper sections may be connected to one another and therefore be considered integrally or permanently connected parts of the compression garment or garment assembly. For purposes of clarity, the terms "lower section" and "upper section" are intended to distinguish the various sections from one another. As such, the lower section is located in surrounding relation to what is generally considered to be the lower portion of the patient's body and extend contiguously from the torso section about the legs and buttocks area. In contrast, the upper section is disposed contiguous to the torso section and extends at least partially upwardly in confronting, force applying relation to the upper lateral portions of the patient's body, the arms, and possibly a part of the back area.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 1 is a perspective view of one preferred embodiment of the compression garment of the present invention represented in a closed orientation which would be assumed when the compression garment is in an operative position on a patient.

FIG. 2 is a front view of the embodiment of FIG. 1 in an open orientation.

FIG. 3 is a sectional view along line 3-3 of FIG. 2.

FIG. 6 is a front view of an additional preferred embodiment of a compression garment structured to be used independently of or as an over garment in combination with the embodiments of FIGS. 1-5.

FIG. 7 is a side view of the embodiment of FIG. 6.

FIG. 8 is a rear view of the embodiment of FIGS. 6 and 7.

FIG. 9 is yet another preferred embodiment of a compressive garment assembly structured to be used independently of or as an over garment in combination with the embodiment of FIGS. 1-5.

FIG. 10 is a side view of the embodiment of FIG. 9.

FIG. 11 is a rear view of the embodiment of FIGS. 9 and 10.

FIG. 12 is a rear view of yet an additional preferred embodiment of an outer compression garment for a female patient of the present invention.

FIG. 13 is a front view of the embodiment of FIG. 12.

FIG. 14 is a side view of the embodiment of FIGS. 12 and 13.

FIG. 14A is a partially cutaway view of the embodiment of FIG. 14 wherein the patient is in a different orientation.

FIG. 15 includes a descriptive legend representative of the different portions of the embodiment of compression garments of FIGS. 12-14A and 16-18 and is indicative of the structuring which results in different degrees of compressive force being exerted on the corresponding parts of the body.

Like reference numerals refer to like parts throughout the several views of the drawings.

DETAILED DESCRIPTION OF THE PREFERRED EMBODIMENT

Figure 5:
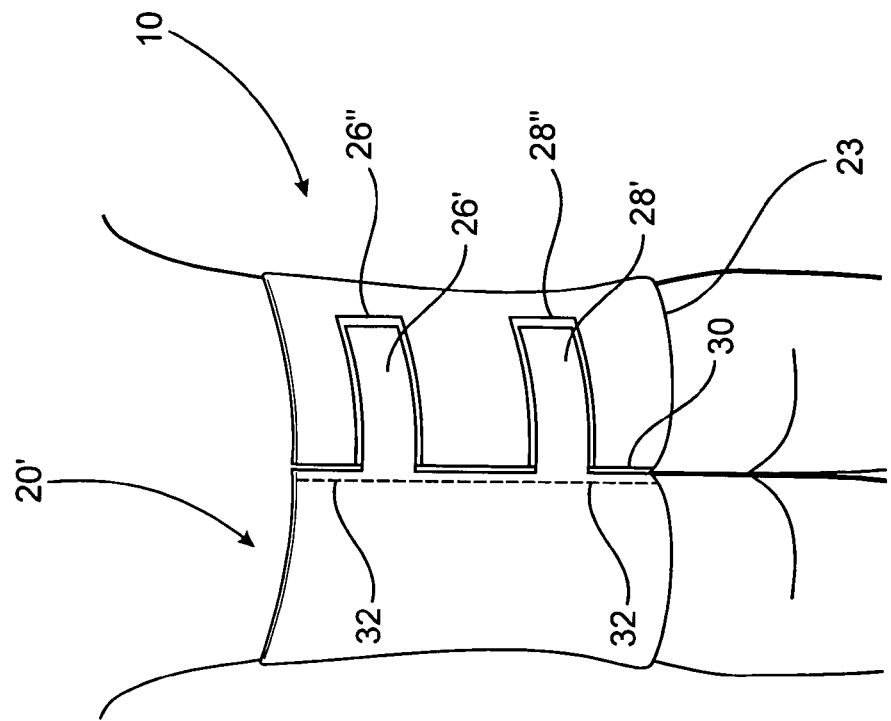
FIG. 5 is a rear perspective view showing details of a closure assembly associated with the embodiment of FIGS. 1 through 4.
Figure 4:
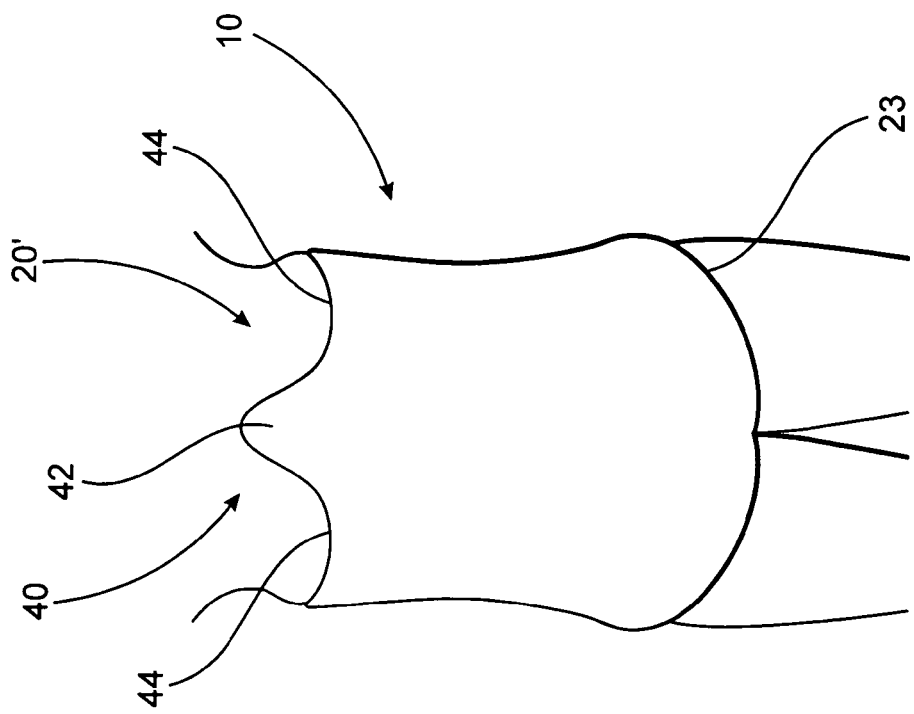
FIG. 4 is a front perspective view of yet another embodiment of the compression garment of the present invention disposed in an operative position and in a closed orientation on a female patient.

As represented in the accompanying Figures, the present invention is directed to a compression garment generally indicated as 10 which is selectively disposable between a closed orientation as represented in FIGS. 1, 4 and 5 and an open orientation as represented in FIG. 2. The compression garment 10 includes structural and operative features which facilitate its use in the treatment of post operative patients involved in various type of body contouring surgery. In particular the compression garment 10 is structured to apply appropriate compressive forces to the surgically affected portion of the patient's body and in particular the torso portion as specifically represented in FIGS. 4 and 5.

In modern day surgical procedures, lipoplasty or other body contouring surgical procedures may affect the torso of a patient's body in generally a "360° range" in order to accomplish a more complete sculptured appearance. Therefore, the compressive forces applied to the patient on a post operative basis are preferably applied substantially to the entirety or at least a majority of the torso when the compression garment 10 is correctly disposed in an operative position.

As set forth above, the operative position is more specifically defined and/or comprises the disposition thereof in the closed orientation of FIGS. 1, 4 and 5, wherein the garment 10 substantially surrounds and forcibly engages indicated portions of the torso. For purposes of clarity, the affected parts of the torso may include the area substantially adjacent or contiguous to the breast area of the patient and extending therefrom down to and over the hip area. As such, the compression garment 10 covers and/or overlies, as well compressively engages, the rib cage and iliac crest of the patient, as represented in FIGS. 4 and 5.

More specific structural features of the embodiment of FIGS. 1-5 include a base or core generally indicated as 12 formed from a flexible, compressible material. The material from which the core or base 12 is formed is preferably polystyrene foam of sufficient flexibility and compressibility to apply the appropriate pressure to various portions, specifically including the torso, of the user's body. Compressive forces will thereby be applied to both the soft tissue portions to the abdomen or back area as well as to the bony prominences such as the rib cage, iliac crest, etc. Accordingly in order to avoid any abrasions, bruising, etc., the flexibility, resiliency, and/or compressibility of the core or base 12 will serve to apply a relatively lesser amount of compressive force to the bony prominences and a relatively greater compressive force or pressure to the soft tissue portions of the torso. As such, the compression garment 10 of the present invention when disposed in the operative orientation as represented in FIGS. 1, 4 and 5 and further when in the closed orientation as also represented in these Figures, will reduce post operative pain and serve to diminish swelling and the avoidance of fluid accumulation or "seroma".

Additional structural features include a cover assembly generally indicated as 14 comprising a first or inner cover member 16 and a second or outer cover member 18, respectively disposed in overlying, covering relation to the inner surface or face 12' and outer surface or face 12" of the core or base 12. As such, each of the first and second cover members 16 and 18 may be formed from a cotton based or other appropriate material. Such material should also have non-allergenic properties or be otherwise treated to facilitate compatibility with the skin of the patient. This is especially true when the compression garment 10 is worn by the patient for an excessive period of time of up to and including approximately thirty days. Further, the first and second cover members 16 and 18 may be of a one piece sleeve like construction disposed in totally enclosing relation to the base or core 12. Alternatively, the first and second cover member 16 and 18 may be connected at one or more locations such that even the upper and lower peripheral portions 20 and 22, respectively of the base or core 12 are covered by the cover assembly 14.

Yet additional structural features of the embodiments of FIGS. 1-5 of the compression garment 10 include a closure assembly generally indicated as 24. The closure assembly 24 includes at least one, but more practically a plurality of elongated closure member pairs as at 26 and 28. Each of the closure member pairs 26 and 28 include elongated straps, belts or other structures defining the closure members 26', 26" and 28', 28". As clearly represented in FIG. 2, each of the elongated, closure member pairs 26 and 28 include one of the closure members 26' and 28' extending outwardly from one longitudinal end 30. The opposite, corresponding closure members 26" and 28" are mounted or affixed to the surface of the outer or second cover member 18 contiguous or adjacent to the other longitudinal end 32. Further, each of the closure members 26', 26" and 28', 28" of the closure member pairs 26 and 28 may be structured to accomplish a removable but secured connection with one another so as to maintain the compression garment 10 in the closed orientation of FIGS. 1, 4 and 5. Therefore each of the closure member pairs 26 and 28 may be formed from hook and loop type fasteners which facilitate the secure but easily separable connection of the closure member pairs 26 and 28 from one another.

As set forth above, when in the closed orientation and in the operative position substantially surrounding the torso of the patient, a compressive force is applied to the underlying portions of the user's body. Such compressive force may be at least partially varied or adjusted by positioning the closure member pairs 26 and 28 such that the opposite longitudinal ends 30 and 32 are brought into substantial alignment with one another. However, it is emphasized that the substantially aligned relation of the opposite ends 30 and 32, when the base 12 and/or compression garment 10 is in the closed orientation, comprises the opposite ends 30 and 32 being contiguously or adjacently disposed relative to one another or even disposed in a partially spaced relation to one another. Further the opposite ends 30 and 32 may be considered in substantial alignment with one another when they are at least partially and variably overlapping one another, as represented in phantom lines in FIG. 5. The degree of overlapping engagement between the ends 30 and 32 as well as the other positions of alignment will be dependent on the size and shape of the patient and will, at least to some extent, determine the amount of compressive force applied to the surrounded portion or torso of the patient. Obviously, the "tighter" the core or base 12 is disposed about and in confronting engagement with the torso of the patient, the greater the compressive force being applied to the torso. Therefore, the amount of compressive force applied to the patient may be considered to be variable in that elongated closure members 26',26" and 28',28" of the closure member pairs 26 and 28 may be variably positioned relative to one another so as to vary the overlapping engagement, and/or spacing of the opposite ends 30 and 32 relative to one another.

Yet additional structural features which at least partially distinguish the embodiment of FIGS. 1-3 from that of FIGS. 4 and 5 is the provision of an upper peripheral portion 20' having an at least partially "scalloped" configuration generally indicated as 40 and represented in FIG. 4. The scalloped configuration 40 is meant to accommodate and at least partially conform to the more pronounced breast area of a female patient. As such, the scalloped configuration 40 is disposed and configured to facilitate a comfortable fit while still maintaining the application of the preferred and appropriate compressive force to the torso of the patient, specifically to the area adjacent the breast portion of the female patient. More specific structural details of the scalloped configuration 40 include an upwardly extending or protruding portion 42 located between oppositely disposed, spaced apart recessed portions 44. As also set forth above, the embodiment of FIGS. 4 and 5 of the compression garment 10 respectively represent a front view and rear view thereof. As such, it is indicated that the scalloped configuration 40 applies more prominently to the frontal portion of the compression garment 10, wherein the upper peripheral portion 20' of the rear part of the compression garment 10 is substantially equivalent to the embodiment of FIGS. 1-3.

Accordingly the embodiments of FIGS. 4 and 5 are primarily, but not exclusively, directed for use by a female patient having a more prominent breast area. In contrast, the embodiment of FIGS. 1-3 is primarily, but not exclusively, structured for use by a male patient, typically having a less prominent breast area. It is further emphasized that the primary difference between the embodiments of FIGS. 1-3 and the embodiment of FIGS. 4 and 5 is the aforementioned and described scalloped configuration 40 at the upper peripheral portion 20' of the core or base 12 and/or compression garment 10. For purposes of clarity, the upper peripheral portions 20, 20' of the embodiments of FIGS. 1-3 and 4 and 5 respectively are located substantially opposite to the lower peripheral portion 23 when the compression garments 10 are in the operative position on a patient as represented in FIGS. 4 and 5 concurrently to the core or base 12 being disposed in the closed orientation as represented in FIGS. 1, 4 and 5.

Yet additional preferred embodiments of the present invention are represented in FIGS. 6-11 and comprise an outer compression garment, which may be dimensioned and configured to facilitate its use by a female patient, as at 100, or a male patient, as at 100'. As emphasized in greater detail hereinafter, the outer compression garment 100, 100' may be used in combination with and in overlying relation to an undergarment such as, but not limited to, the compression garment as represented in FIGS. 1-5. Moreover, whether used independently of or in combination with an undergarment, the outer garments 100, 100' each include a base 102 formed from a flexible, compressible material, such as a compressive foam material. The compressive foam material has sufficient flexibility and compressive characteristics to apply appropriate pressure to various portions of the torso of the male or female patient, when operatively disposed thereon. As also set forth above with regard to the embodiment of FIGS. 1-5, the compressive forces exerted on the female or male patient's body by the outer compressive garment 100, 100' and more specifically the base 102, will be applied to both the soft tissue portions as well as the bony prominences. The soft tissue portions include the abdomen, back area, underarms, etc., wherein the bony prominences such as the rib cage, iliac crest, etc. In order to avoid any abrasions, bruising, etc. the flexibility, resiliency and compressibility of the foam material from which the base 102 of the garments 100, 100' are formed will serve to apply a relatively a lesser amount of compressive force to the bony prominences. In contrast, a relatively greater compressive force or pressure will be applied to the soft tissue portions of the torso. The intended result will be a reduction in post operative pain and a concurrent lessening of the swelling and fluid accumulation.

More specifically, and with regard to FIGS. 6-8 and 9-11, each base 102 of the garments 100, 100' include a first or upper end generally indicated as 104 and 104' and a second or lower end 106 and 106'. The base 102 of each of the garments 100, 100' extends continuously between the corresponding first and second ends and is dimensioned and configured to substantially surround the torso of the patient when in the operative position as represented in FIGS. 6-11. Each of the first ends 104 and 104' includes a frontal portion 108 and 108' and a rear portion 110 and 110', respectively. Similarly, each of the second or lower ends 106 includes a frontal portion 112 and 112' respectively and a rear portion 114 and 114' respectively.

Therefore, as clearly represented in the corresponding FIGS. 6-8 and 9-11, the female compressive garment 100 and the male compression garment 100' are each dimensioned and configured to substantially conform to the body of a female patient and a male patient, respectively.

With primary reference to FIGS. 6-8, the outer compression garment 100 includes a frontal portion 108 of the upper first end 104 having a substantially scalloped configuration extending across at least a majority of the length thereof between oppositely disposed lateral portions 115. The scalloped configuration of the frontal portion 108 is disposed and dimensioned to substantially conform to the lower pectoral region or breasts of the female patient. As such, an appropriate force and at least partial support is applied to this region. In contrast, the frontal portion 108' of the first or upper end 104' of the male outer compression garment 100' has a substantially linear configuration extending along or across at least a majority of the distance between the lateral portions 115. Accordingly, the frontal area 108' of the first or upper end 104' is also disposed in aligned and/or at least partially supporting relation to the lower pectoral region of the male patient. As best represented in FIGS. 8 and 11, the rear portion 110 and 110' of the first or upper end 104 and 104' each include a substantially convergent or downwardly directed, generally U-shaped configuration as the rear portion 110 extends between and in interconnecting relation between the lateral portions 115.

Further, in each of the male and female compression garments 100 and 100', the base 102, 102' includes the aforementioned lateral portions 115 extending outwardly from the corresponding frontal portions 108, 108' and rear portions 110, 110' a sufficient distance to be disposed in alignment with or overlying relation to the underarm portions and/or "armpit" of the patient. As such, the lateral portions 115 are integrally formed with the remainder of the base 102, 102' and extend in interconnecting relation between the front and rear portions 108, 108' and 110, 110'. Of further note is that the longitudinal dimension of each of the lateral portions of each of the garments 100, 100' are sufficient to extend upwardly in substantially aligned, overlying relation with an underarm portion of the corresponding patient and/or in aligned, relation with the "armpit" of the corresponding patient.

Rear portions 110, 110' and 114, 114' of the base 102, 102' are at least partially or generally structured to have a similar configuration. As such, the rear portion of the upper end 110 and 110' both have an at least partially or generally U-shaped configuration which is defined by the periphery of the rear portions 110, 110' extending continuously in a downwardly curved or convergent manner from the lateral portions 115.

As also represented in FIGS. 8 and 11, the rear portion 114, 114' of the second or lower end 106, 106' includes a substantially scalloped configuration. The scalloped configuration of each of the rear portions 114, 114' are disposed and dimensioned to substantially conform to the upper buttocks area of the respective female and male patients. It is further noted that the dimensions, configurations, and dispositions of the frontal and rear portions 108, 108' and 110, 110' as well as the frontal and rear portions 112, 112' and 114, 114' of the second or lower end 106 are not mere design choices but instead are intended to apply appropriate compressive forces to both the soft tissue and hard tissue portions of the patient's body in a manner which serves to overcome swelling and reduce pain, as set forth above.

As also best represented in FIGS. 8 and 11, each of the male and female outer compressive garments 100, 100' includes a closure assembly generally indicated as 124. Accordingly, the closure assembly 124 is substantially equivalent in structure and operation to the closure assembly 24 as described above with specific reference to the embodiments of FIGS. 1-5. Therefore, closure assembly 124 is connected to corresponding opposite free ends 130 and 132. As also set forth above, the degree of overlapping engagement between the ends 130 and 132 is at least partially dependent on the size and shape of the patient. Accordingly, such overlapping engagement will also be determinative of the amount of compressive force applied to the various portions of the torso and/or other portions of the patient's body to which compressive forces are applied by the garments 100, 100'. As a result, the amount of compressive force applied to the patient may be considered to be variable in that the various parts of the closure assembly 124 can be variably positioned relative to one another so as to vary the overlapping engagement and/or spacing of the oppositely disposed free ends 130 and 132, relative to one another.

Figure 16:
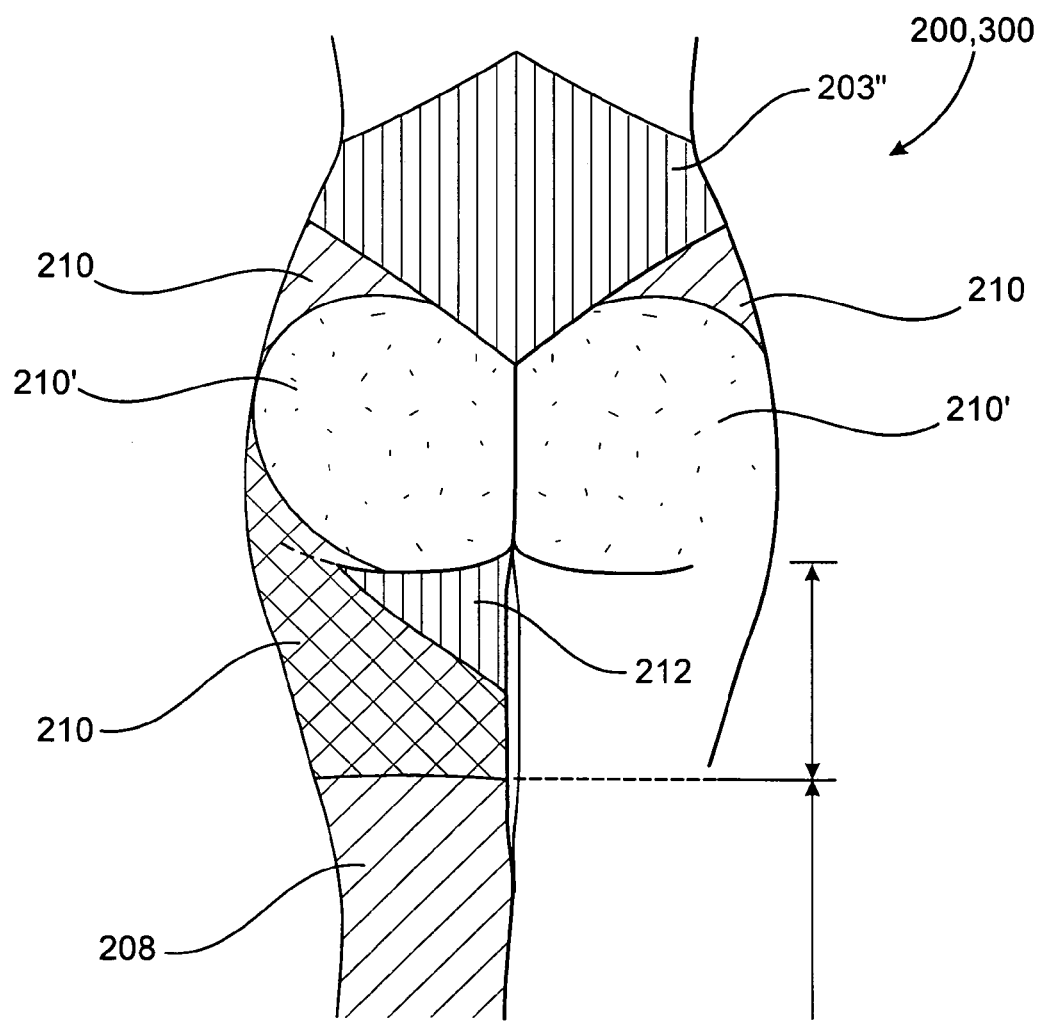
FIG. 16 is a rear view in partial cutaway of the embodiment of FIGS. 12-14.
Figure 18:
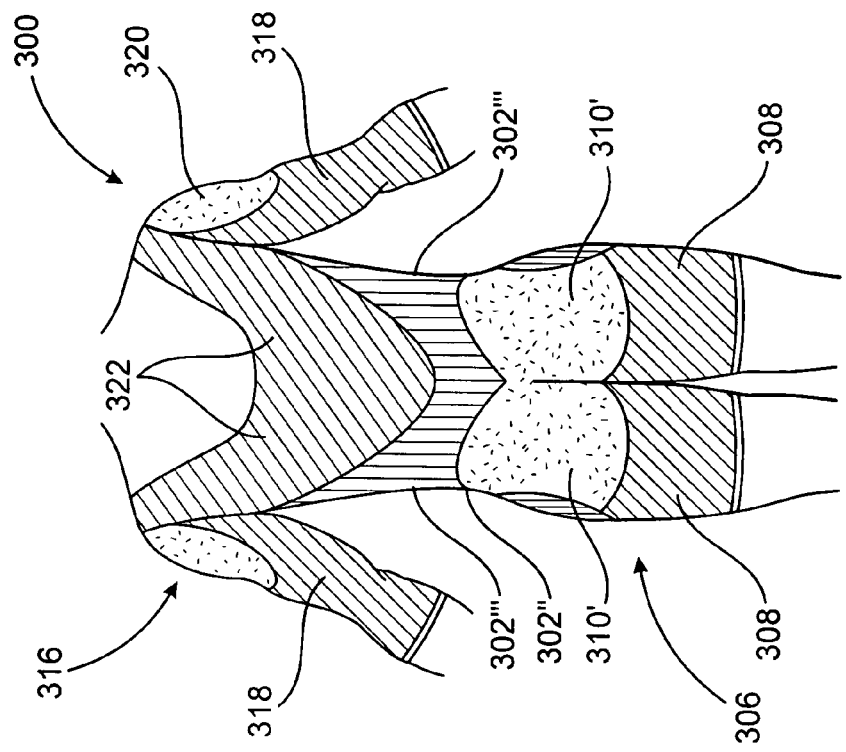
FIG. 18 is a rear view of the embodiment of FIG. 17.
Figure 17:
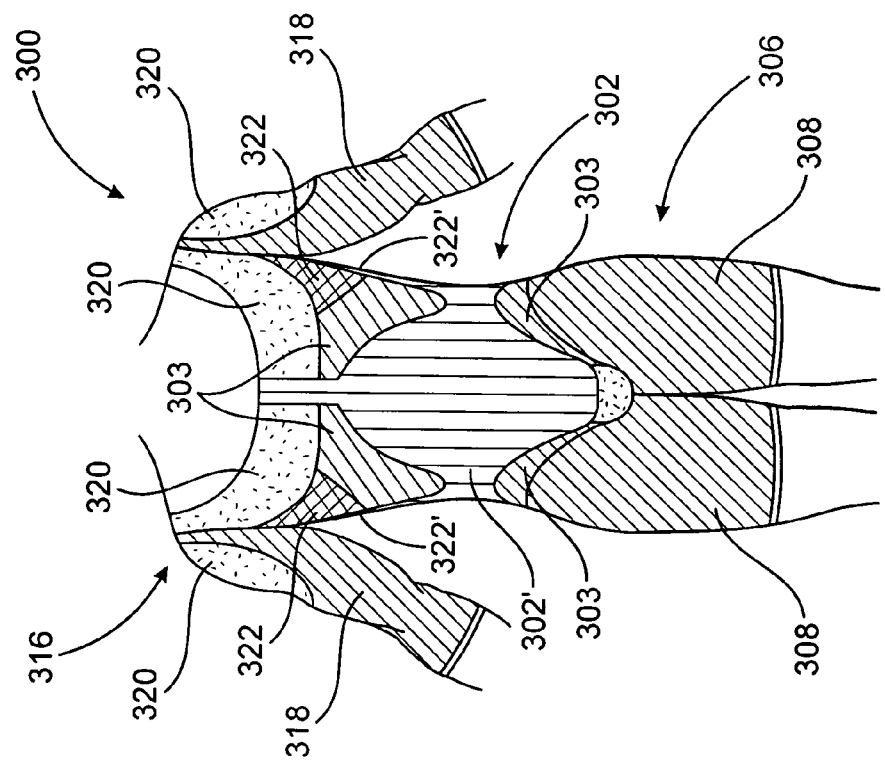
FIG. 17 is a front view of yet another preferred embodiment of the outer compression garment which is dimensioned and configured for adaptation for use and wearing by a male patient.

Yet additional preferred embodiments of the compression garment of the present invention are represented in FIGS. 12-18. More specifically and as set forth in greater detail hereinafter, outer garment or garment assembly 200 represented in FIGS. 12-14A is structured for use on the body of a female post operative patient. As represented in FIGS. 17 and 18, the outer compression garment generally indicated as 300 is primarily dimensioned and configured for use on a male post operative patient. As such the different embodiments of FIGS. 12-15 and 17-18 have substantially similar or in some cases identical operative features, but may differ in dimension, configuration and structuring in order to adapt to a better fit of the female torso and male torso.

Accordingly, the outer compression garments 200 and 300, both include a plurality of sections, wherein each section includes a plurality of segments. The plurality of segments associated with each of the various sections are cooperatively disposed and structured to apply different degrees of compressive force to the corresponding body parts or portions of the patient with which they confront, overlie or otherwise are directly associated. As will be emphasized in greater detail hereinafter, the different degrees of compressive force exerted on corresponding body portions by the plurality of segments are schematically indicated by a descriptive reference legend represented in FIG. 15. As indicated, the structure of the plurality of segments of each section may vary in order to apply the different degrees of compressive force to the corresponding body portions.

With more specific reference to FIG. 15, the represented legend indicates a plurality of different material structures such as preferably three or more. As such, the structuring of the material of each of the indicating segments A-D provide a lesser to greater compressive force on the corresponding body portion. Such a variance in compressive force may be accomplished by regulating the thinness or thickness of the material, wherein the material may include, but not be limited to, foam or other appropriate material capable of exerting a compressive force on the corresponding body portion. More specifically, schematic representation A may represent the structuring of at least some segments of the various sections of the outer compression garments 200, 300 having the thinnest dimension. As such, these segments will exert the least degree of compressive force on the body portion. In contrast, the represented reference legend D is representative of those segments, of each of the body sections, which are structured to exert the greatest degree of compressive force on the corresponding body part and as such may be structured to have the thickest dimension. Alternately, the plurality of segments having the structural or reference indication A-D may be formed from a different materials, each of which has an inherent structuring which applies a different compressive force to the corresponding body portion.

With primary reference to FIGS. 12-14A, the outer compression garment or garment assembly 200 includes a torso section 202 having a plurality of first segments 203, 203' and 203". More specifically, the segment 203' represents an abdominal segment disposed in overlying and/or confronting relation to the abdomen of the patient. In addition, the plurality of segments 203 at least partially defining the torso section 202 comprises a back segment 203". The abdominal segment 203' and the back segment 203" may be integrally interconnected by means of two, spaced apart segments 203'''.

As also represented, the remainder of the plurality of segments 203 which at least partially define the torso section 202 may be structured to exert different degrees of compressive force on the corresponding body portions as indicated by the reference material legend of FIG. 15. Moreover, at least some of the remainder of the plurality of segments 203 may be structured to exert different degrees of compressive force on the body as compared to one another. The body part being variably compressed is at least partially dependent on the surgical procedure performed on the patient, the condition of the patient and possibly other factors.

With further regard to the embodiments of FIGS. 12-14A, outer, female compression garment 200 also includes a lower section generally indicated as 206 which is dimensioned and configured to cover at least the upper legs of the patient as well as the hips and/or buttocks area, as clearly represented. Similar to the torso section 202, the lower section 206 comprises a plurality of pressure applying segments 208 overlying or confronting the legs, 210 as well as at least the portion of the buttocks and hip area of the patient. In addition the gluteal segments 212 are disposed in substantially overlying and at least partially aligned relation with the gluteal crease of the patient as outlined in greater detail in FIG. 16. For purposes of clarity, the gluteal crease is represented at least partially in phantom lines and is the anatomical junction or line existing between the buttocks and upper, contiguous portion of the leg.

In at least one preferred embodiment, the gluteal segments 212 extend along at least a third of the length of the gluteal crease as represented. Moreover, the gluteal segments 212 are structured to exert a greater compressive force on the corresponding gluteal area of the patient than at least some of the remainder of the plurality of second segments 208, 210, etc. As also indicated, the plurality of segments 210' (see FIG. 16) overlying a major portion of the buttocks may be structured to exert the least degree of compressive force, wherein the area overlying the lower portion of the legs, as at 208, represent an intermediate compressive force being exerted thereon. As also indicated in the detail of FIG. 16, the plurality of the second segments 210 overlying the upper portion of the leg in the vicinity of the gluteal crease as well as overlying the hips are structured to exert different degrees of compressive force on the respective body portions again with reference to the legend of FIG. 15. It is also noted that the gluteal segments 212 are structured, along with the abdominal segment 203' and back segment 203", to exert the maximum degree of compressive force on the corresponding body portions.

Further with regard to the embodiments of FIGS. 12-14A, the female outer compression garment 200 also includes an upper section generally indicated as 216. Upper section 216 is structured to include a plurality of third segments collectively disposed to cover the arms, shoulders, portions of the back, and lateral or "lats" portions. More specifically, the upper section 216 includes third segments 218 disposed to cover the arm and including segments 218' which overlie and/or confront underarm or tricep area as indicated. The upper section 216 also includes a plurality of third segments 220 disposed in at least partially enclosing and/or confronting relation to the shoulders. The plurality of third segments of the upper section 216 are disposed in at least partially enclosing and/or overlying relation to the back area as at 222 and the lateral portion or "lats" as at 222'. As with the torso section 202 and the lower section 206, the plurality of third segments 218, 218', 220, 222, etc. are cooperatively and collectively structured to exert different degrees of compressive force on the corresponding body portion with which they are associated. Again with reference to the legend of FIG. 15, the greatest degree of compressive force is exerted by the third segments 218' overlying and/or confronting the tricep area of the arm. The third segments 220 overlying the shoulders are structured to exert the least compressive force. The remaining third segments 222 and 222' are structured to exert yet a different degree of compressive on the corresponding body portion as indicated.

With primary reference to the additional preferred embodiment of FIGS. 17 and 18, male compression outer garment 300 includes similar structural and operative features, as set forth above and as described in detail with the embodiment of FIGS. 12-14A. More specifically, the garment or garment assembly 300 includes a torso section 302, a lower section 306 and an upper section 316. Moreover, the torso section 302 comprises a plurality of first segments 302', 302", 303, etc. Similarly, the lower section 306 includes a plurality of second segments 308, 310, 310', etc. The upper section 316 includes a plurality of third segments 318, 320, 322', etc. A plurality of segments of each of the torso section 302, lower section 306 and upper section 316 confront, overlie or directly associated with the corresponding body portions as indicated and are structured to exert different degrees of compressive force on the corresponding body portions. By way of example, the torso section 302 includes an abdominal segment 302', a back segment 302" and a side or waist segments 302'''. As represented in both FIGS. 17 and 18, the waist segments 302''' may extend upwardly beneath the arms of the patient so as to at least partially confront and exert a compressive force on the lateral area or "lats". The torso portion includes a frontal area covered by the segments 303 which are disposed to extend outwardly from the periphery of the abdominal segment 302' and back segment 302".

Similarly the lower section 306 includes a plurality of second segments 308 designed to cover the upper legs, wherein the plurality of second segments 310' cover the buttocks area as indicated. It is also of note that the compression of the outer garment 300 may include the structural configuration as represented in FIG. 16. As such, gluteal segments 212 are included within the lower section 306 so as to extend along and apply at least a determined amount of pressure along the gluteal crease.

Similarly, the upper section 316 includes a plurality of third segments covering the arms as at 318, the "lats" as at 322', the frontal portion of the chest as at 320 and 322'. With reference to the legend of FIG. 15, the various first, second and third segments of the respective torso, lower and upper sections, 302, 306 and 316 may all exert a different, but predetermined, degree of compressive force on the corresponding body portions.

Additional structural features include each of the torso, lower, and upper sections of the each of the garments or garment assemblies 200 and 300 being connected to one another so as to form a unitary garment construction. Alternatively, each of the torso, lower and upper sections of each of the garment or garment assemblies 200 and 300 may be independently placed on the patient, wherein the borders or peripheries thereof are contiguous to one another.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A garment structured to compress predetermined body portions of a post-operative patient, said garment comprising:
    a torso section dimensioned and configured to at least partially enclose the torso portion of the patient's body and comprising an abdominal segment disposed in overlying relation to the abdomen of the patient,
    a lower section disposed beneath said torso section in enclosing relation to at least the upper legs and buttocks of the patient and comprising two gluteal segments each disposed in at least partially confronting relation to the buttock and in aligned relation to a portion of a gluteal crease of the patient,
    an upper section disposed above said torso section in at least partially enclosing relation to the arms and upper lateral portions of the patient and comprising two underarm segments each extending along at least a majority of the length between a corresponding elbow and a corresponding shoulder to a corresponding tricep area of the patient,
    each of said torso, lower and upper sections comprising a plurality of segments cooperatively disposed and structured to apply a plurality of different degrees of compressive force to correspondingly disposed body portions of the patient,
    said abdominal segment, said two gluteal segments and said two underarm segments each structured to apply a greater degree of compressive force to correspondingly disposed parts of the patients body than a remainder of said plurality of segments of respective ones of said torso, lower and upper sections, and
    a remainder of said plurality of segments of each of said torso, lower and upper sections being structured to apply different degrees of compressive force to correspondingly disposed body portions as compared to one another.

2. A garment as recited in claim 1 wherein at least two of said torso, lower and upper sections are connected to one another.

3. A garment as recited in claim 1 wherein at least said torso section is dimensioned and configured to define an outer garment section disposable in overlying relation to at least a portion of an undergarment disposed in at least partially surrounding relation to the patient's body.

4. A garment as recited in claim 1 wherein said torso, lower and upper sections are collectively structured to substantially conform to the body of a female patient.

5. A garment as recited in claim 1 wherein said torso, lower and upper sections are collectively structured to substantially conform to the body of a male patient.

6. A garment as recited in claim 1 wherein said plurality of segments of each of said torso, lower and upper sections are cooperatively structured to apply at least three different degrees of compressive force to the patient's body.

* * * * *